United States Patent [19]
Kim

[11] Patent Number: 5,987,675
[45] Date of Patent: Nov. 23, 1999

[54] SPINAL SUPPORT AND STRETCH PILLOW SYSTEM

[76] Inventor: Susan Young-Sook Kim, 23833 Arroyo Park, No. 1301, Valencia, Calif. 91355

[21] Appl. No.: 09/173,237

[22] Filed: Oct. 15, 1998

[51] Int. Cl.[6] ........................... A47C 27/08; A47C 20/02; A47G 9/00
[52] U.S. Cl. ....................................... 5/632; 5/633; 5/636
[58] Field of Search ................................ 5/632, 630, 633, 5/636, 637, 638, 640; 128/845; 606/240, 242

[56] References Cited

U.S. PATENT DOCUMENTS

| | | |
|---|---|---|
| 1,909,039 | 4/1933 | Bruder . |
| 2,767,410 | 10/1956 | Benson . |
| 3,009,172 | 11/1961 | Eidam ........................................ 5/632 |
| 3,879,775 | 4/1975 | Iwata . |
| 3,924,282 | 12/1975 | Bond . |
| 4,171,549 | 10/1979 | Morrell et al. . |
| 4,193,150 | 3/1980 | Vineberg . |
| 4,501,034 | 2/1985 | Greenawalt ................................ 5/644 |
| 4,665,573 | 5/1987 | Fiore . |
| 4,689,844 | 9/1987 | Alivizatos . |
| 4,741,058 | 5/1988 | Williams et al. . |
| 4,791,687 | 12/1988 | Iwase . |
| 4,843,666 | 7/1989 | Elesh et al. . |
| 4,853,993 | 8/1989 | Walpin et al. . |
| 4,908,894 | 3/1990 | Sanders . |
| 4,955,096 | 9/1990 | Gilroy et al. . |
| 4,977,629 | 12/1990 | Jones . |
| 5,016,303 | 5/1991 | Tanaka et al. . |
| 5,018,790 | 5/1991 | Jay ............................................. 5/653 |
| 5,048,137 | 9/1991 | Rogers . |
| 5,168,590 | 12/1992 | O'Sullivan ................................ 5/636 |
| 5,172,439 | 12/1992 | Farley . |
| 5,279,310 | 1/1994 | Hsien ........................................ 5/636 |
| 5,479,667 | 1/1996 | Nelson et al. ............................. 5/632 |
| 5,528,783 | 6/1996 | Kunz et al. ................................ 5/644 |
| 5,572,753 | 11/1996 | Ruscitto .................................... 5/636 |
| 5,632,050 | 5/1997 | Zajas et al. ............................... 5/632 |

*Primary Examiner*—Alexander Grosz
*Attorney, Agent, or Firm*—Thomas I. Rozsa; Tony D. Chen; Jerry Fong

[57] ABSTRACT

A spinal support and stretch pillow system offers a distinct, adjustable support for sleeping in either a supine position or a lateral-lying position. The spinal support and stretch pillow system can be laid over a conventional mattress or a floor. The spinal support and stretch pillow system is comprised of a bottom liner pad, a cervical and spinal support pad, a height adjustment pad, an adjustable shoulder support, an adjustable thoracic and lumbar support pad, and a top support pad. The bottom liner pad is used as a container to retain the components of the spinal support and stretch pillow system and for covering the user's legs and feet. The cervical and spinal support pad has a U-shaped cutout portion for allowing the head of the user to fall back and stretch the neck of the user. The height adjustment pad is positioned underneath a cervical section of the cervical and spinal pad for adjusting the height of the cervical section. The adjustable shoulder support pad is located adjacent to the cervical and spinal support pad for supporting a shoulder region of a spinal section of the cervical and spinal support pad. The adjustable thoracic and lumbar support pad is positioned underneath a thoracic and lumbar region of the spinal section for further supporting the back of the human body. The top cover support pad is positioned over the cervical and spinal support pad. The top support pad has one end folded over against itself to retain an adjustable neck support member and the other end folded underneath against itself to retain an adjustable knee support member.

23 Claims, 3 Drawing Sheets

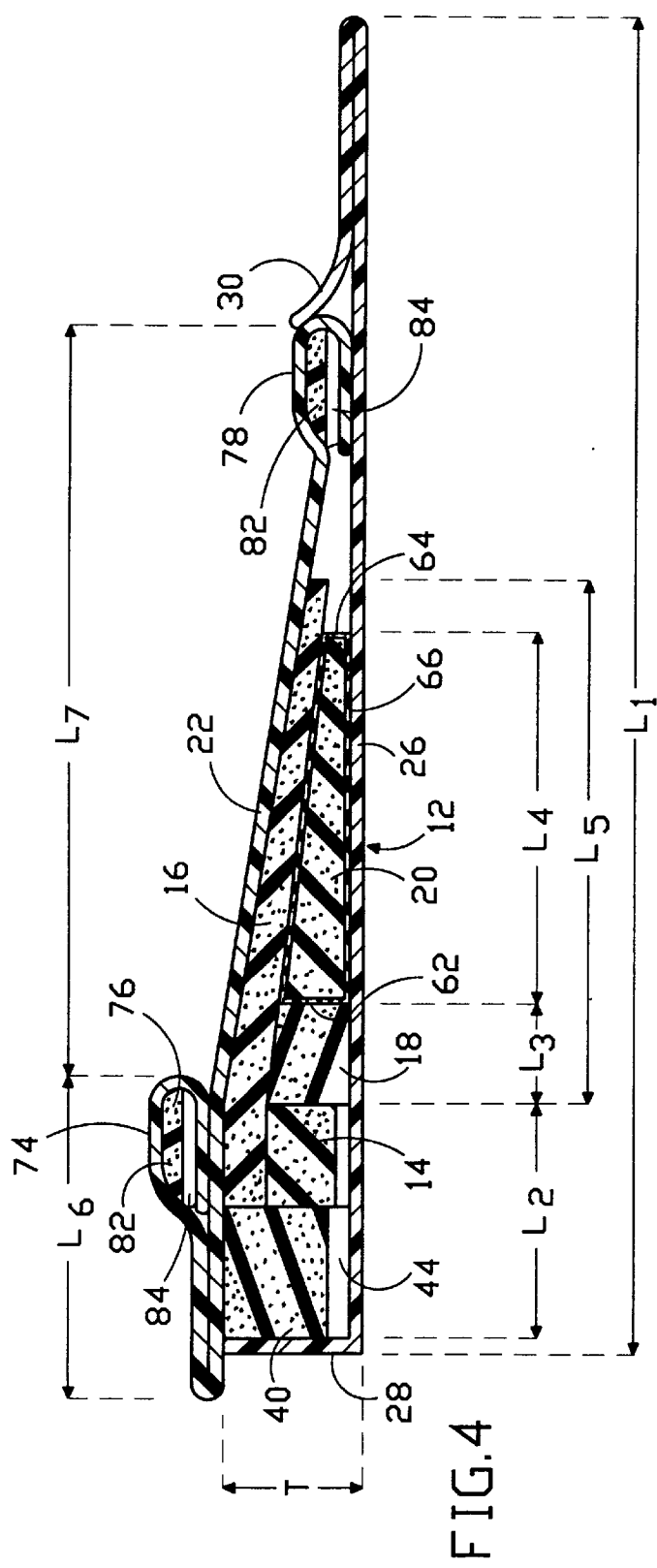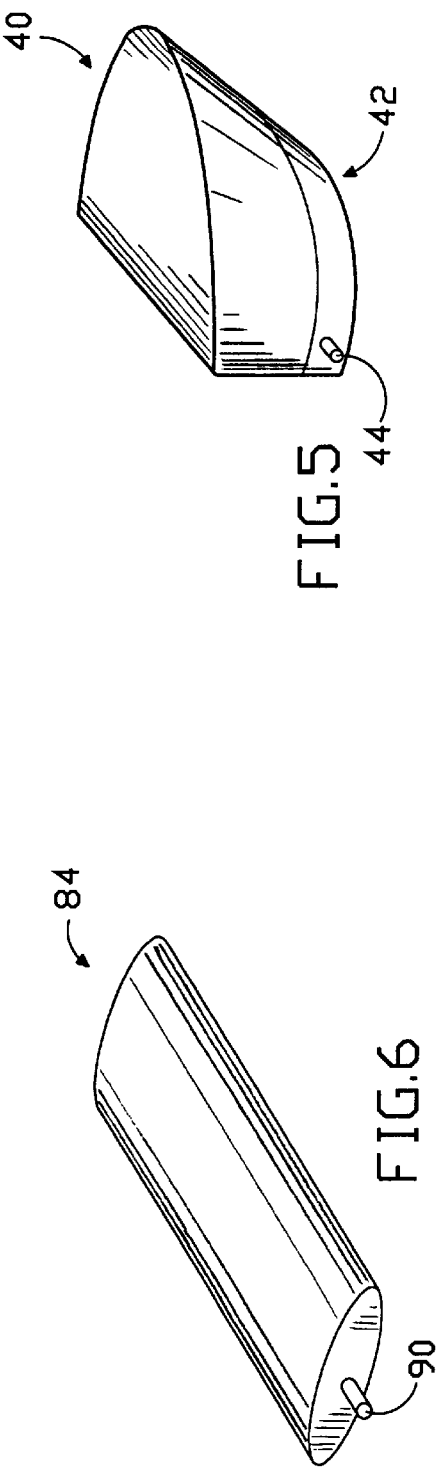

SPINAL SUPPORT AND STRETCH PILLOW SYSTEM

BACKGROUND OF THE INVENTION

1. Field of the Invention

The present invention generally relates to the field of resilient support pads. More particularly, the present invention relates to the field of resilient support pads for passively treating cervical, thoracic and lumbar alignment disorders and correcting or preventing poor posture.

2. Description of the Prior Art

Specifically, mild forms of poor posture are very common in people. These mild forms of poor posture produce back and neck discomfort. A wide variety of pillow or therapeutic devices are designed to alleviate the pain and discomfort associated with the poor posture. One such device relates to pillow supports for easing neck and back strain while a person is sleeping or resting on his/her back (the supine position) or resting on his/her side. These pillow supports have many configurations and use a wide variety of padding and contouring materials, such as foam, polyester filaments, goose down, and the like, in order to provide relief to the user.

The following twenty-four (24) prior art patents are found to be pertinent to the field of the present invention:

1. U.S. Pat. No. 1,904,039 issued to Bruder on Apr. 18, 1933 for "Body Exercising Apparatus" (hereafter the "Bruder patent");
2. U.S. Pat. No. 2,767,410 issued to Benson on Oct. 23, 1956 for "Mattress With Foot Hold" (hereafter the "Benson patent");
3. U.S. Pat. No. 3,879,775 issued to Iwata on Apr. 29, 1975 for "Cushion" (hereafter the "'775 Iwata patent");
4. U.S. Pat. No. 3,924,282 issued to Bond on Dec. 9, 1975 for "Therapeutic Prop-Like Support For Hemiside Reclining Persons" (hereafter the "Bond patent");
5. U.S. Pat. No. 4,171,549 issued to Morrell et al. on Oct. 23, 1979 for "Cushion Ensemble And Method Of Arranging Cushions To Provide The Same" (hereafter the "Morrell patent");
6. U.S. Pat. No. 4,193,150 issued to Vineberg on Mar. 18, 1980 for "Elevated Mattress" (hereafter the "Vineberg patent");
7. U.S. Pat. No. 4,501,034 issued to Greenawalt on Feb. 26, 1985 for "Inflatable Pillow" (hereafter the "Greenawalt patent");
8. U.S. Pat. No. 4,665,573 issued to Fiore on May 19, 1987 for "Contoured Body Support Structure" (hereafter the "Fiore patent");
9. U.S. Pat. No. 4,689,844 issued to Alivizatos on Sep. 1, 1987 for "Convertible Body Supporting Pads" (hereafter the "Alivizatos patent");
10. U.S. Pat. No. 4,741,058 issued to Williams et al. on May 3, 1988 for "Convoluted Support Pad For Prevention Of Decubitus Ulcers And Apparatus For Making Same" (hereafter the "Williams patent");
11. U.S. Pat. No. 4,791,687 issued to Iwase on Dec. 20, 1988 for "Mattress With Support" (hereafter the "'687 Iwase patent");
12. U.S. Pat. No. 4,843,666 issued to Flesh et al. on Jul. 4, 1989 for "Pillow Mattress" (hereafter the "Elesh patent");
13. U.S. Pat. No. 4,853,993 issued to Walpin et al. on Aug. 8, 1989 for "Adjustable Body Positioner" (hereafter the "Walpin patent");
14. U.S. Pat. No. 4,908,894 issued to Sanders on Mar. 20, 1990 for "Adjustable Pillow" (hereafter the "Sanders patent");
15. U.S. Pat. No. 4,955,096 issued to Gilroy et al. on Sep. 11, 1990 for "Anatomically Contoured Convoluted Foam Pad" (hereafter the "Gilroy patent");
16. U.S. Pat. No. 4,977,629 issued to Jones on Dec. 18, 1990 for "Portable Inflatable Patient Assist Apparatus" (hereafter the "Jones patent");
17. U.S. Pat. No. 5,016,303 issued to Tanaka et al. on May 21, 1991 for "Cervical And Head Support Pillow" (hereafter the "Tanaka patent");
18. U.S. Pat. No. 5,018,790 issued to Jay on May 28, 1991 for "Customized Seat Cushion" (hereafter the "Jay patent");
19. U.S. Pat. No. 5,048,137 issued to Rogers on Sep. 17, 1991 for "Edge-Shear Reduction In Body Support Foam Pads" (hereafter the "Rogers patent");
20. U.S. Pat. No. 5,168,590 issued to O'Sullivan on Dec. 8, 1992 for "Therapeutic Pillow Cover Having Compartments For Receiving Hot/Cold Packs And/Or Pillow Insert Supports" (hereafter the "O'Sullivan patent");
21. U.S. Pat. No. 5,172,439 issued to Farley on Dec. 22, 1992 for "Therapeutic Mattress Overlay And Method Of Forming And Using The Same" (hereafter the "Farley patent");
22. U.S. Pat. No. 5,279,310 issued to Hsien on Jan. 18, 1994 for "Spinal Column Correction Device" (hereafter the "Hsien patent");
23. U.S. Pat. No. 5,528,783 issued to Kunz et al. on Jun. 25, 1996 for "Inflatable Head And Torso Support" (hereafter the "Kunz patent"); and
24. U.S. Pat. No. 5,572,753 issued to Ruscitto on Nov. 12, 1996 for "Pillow Case Head Cover" (hereafter the "Ruscitto patent").

The Bruder patent discloses a body exercising apparatus which comprises a supporting means, a head rest and a foot rest.

The Benson patent discloses a mattress with a foothold. The mattress is made out of foam material and encased by a fabric material.

The '775 Iwata patent discloses a cushion. It comprises a main structural part with three compartments and two gusset cloths. The main structural part is formed from two covering cloths, for example, a lower and an upper, which are stitched together by a continuous stitched line peripherally along the four held edges and two transverse stitched lines to form three tandem arranged compartments which are stuffed with cushionable material, for example, elastic foam.

The Bond patent discloses a therapeutic prop-like support for hemiside reclining persons. It comprises an elongated narrow web-like draw-sheet that is superimposed upon the bedsheet at a selectable angle transversely to the bed lengthwise central axis. The prop-like support comprises a pair of substantially parallel primary sleeves carried at and extending laterally along the drawsheet elongated topside. The respective primary-sleeves are adapted to removably accommodate a bolster which firmly and comfortably abuts the upper-spinal backside of a hemiside reclining person to beneficially maintain him on the leftward or rightward hemiside depending upon the employment of the sleeves.

The Morrell patent discloses a cushion ensemble and method of arranging cushions to provide the same. It comprises a first large wedge-shaped cushion, a second smaller wedge-shaped cushion, and a third wedge-shaped cushion. The first and second cushions are arranged in a common plane so that their upwardly facing sides converge downwardly toward each other. The third wedge-shaped cushion is placed on the generally upwardly facing, inclined surface of the first cushion to serve as a shoulder, neck, or back rest.

The Vineberg patent discloses an elevated mattress for placing on the top of a conventional mattress for elevating the head and thorax of a patient.

The Greenawalt patent discloses an inflatable pillow. It comprises one or more elements for receiving the neck or cervical region of a person lying on the pillow and another, adjacent element for receiving the person's head.

The Fiore patent discloses a contoured body support structure. It comprises an upper surface contoured to maintain the spine of a person lying horizontally on the mattress in the proper curvature regardless of whether the person is lying in the supine, prone, or side portion. The upper surface has a convex shape in each of the lumbar and knee regions and has a concave depression in the sacral region with reduced tapering end portions from the lumbar and knee regions to the ends of the support.

The Alivizatos patent discloses convertible body supporting pads. The support pads are formed from flexible fabric closed covers of generally rectangular configuration forming a chamber which is filled to approximately 50% of its normal maximum volume with relatively small expanded polystyrene beads.

The Williams patent discloses a convoluted support pad for prevention of decubitus ulcers and apparatus for making same. The pad has a head and a foot supporting section, each in the form of a convoluted, checker board pattern of rows of peaks separated by depressions.

The '687 Iwase patent discloses a mattress with support members along the length of the mattress.

The Elesh patent discloses a pillow mattress.

The Walpin patent discloses an adjustable body positioner. It comprises a foundation which is comprised of top and bottom substructures. The foundation includes an acute angle edge and a concave widthwise contour. The top and bottom substructures are joined at the acute angle edge by a hinge means. An insert is formed to allow it to be replaceably interleaved between the top and bottom substructures.

The Sanders patent discloses an adjustable pillow. It comprises an adjustable neckroll section and a head support section. The neckroll section has a foam rubber pad rolled into a spiral roll and housed within a cylindrical case. The case can be opened to allow the pad to be removed and trimmed. The diameter of the neckroll can thus be adjusted to correspond to the contour of the user's neck. The head support section has an outer section and an inner section. The thickness of the outer section may be adjusted by adding or removing filler material. The thickness of the inner section may be adjusted by adding or removing inlays in a stacked arrangement.

The Gilroy patent discloses an anatomically contoured convoluted foam pad.

The Jones patent discloses a portable inflatable patient assist apparatus. It is a multi-chambered pad which is positioned on a bed wherein the bedridden person would make contact with the pad. The pad has first and second inflatable chambers positioned adjacent the bed, which would overlap down a double longitudinal axis. Each chamber has its own inlet for pressurized air to be pumped for selectively inflating that particular chamber.

The Tanaka patent discloses a cervical and head support pillow. It comprises an outer pillow covering with a top half and a bottom half, a contoured foam core, and three foam inserts which include a first height insert, a second height insert and a V-shaped insert.

The Jay patent discloses a customized seat cushion. It comprises securable removable supports which are used in combination with a shaped tray and a pad containing a fluid filling material. The supports are fastened to selected contours of the shaped tray, and the surface presented by the supports and shaped tray are covered by the pad which is fastened to the exposed surfaces of the tray and pads.

The Rogers patent discloses an edge-shear reduction in body support foam pads. The body support has a top opening.

The O'Sullivan patent discloses a therapeutic pillow cover having compartments for receiving hot/cold packs and/or pillow insert supports.

The Farley patent discloses a therapeutic mattress overlay and method of forming and using the same. The mattress has a hump for supporting the knees of an individual.

The Hsien patent discloses a spinal column correction device. It comprises a head rest, a lumbar rest, and a bottom rest. The head rest has a first raised support, a second raised support formed with a recess at the intermediate portion, a groove between the first raised support and the second raised support, a triangular region extending downwardly from the second raised support, and a Velcro strap at the lower edge of the head rest. The lumbar rest has a Velcro strap at the upper edge and the lower edge, a swollen region at the intermediate portion, a spine line at the center, a triangular region at the upper portion, and two recesses at the lower portion for receiving the hips of a user. The bottom rest has two recesses for receiving the feet of a user and a swollen region between the two recesses for resting the feet, whereby the device may effectively correct the spinal column of a user.

The Kunz patent discloses an inflatable head and torso support. It comprises a wedge shaped inflatable air bladder, a source of pressurized air, and air hose and valves for the controlled inflation and deflation of the air bladder.

The Ruscitto patent discloses a pillow case head cover made from a single piece of material folded and joined in a method so as to create two primary envelopes.

Many of these support devices are designed to offer support of the cervical or neck area of the user, and also provide a comfortable area on which the user may rest his/her head. However, none of the prior support devices teaches a spinal support and stretch pillow system for stretching the entire spine and correcting poor posture problems while a user is sleeping in the supine position or the lateral-lying position. It is desirable to provide a spinal support and stretch pillow system for passively treating certain spinal curvature disorders, including cervical, thoracic and lumbar disorders. It is also desirable to provide a spinal support and stretch pillow system for supporting a person's body in a manner required by his or her particular condition and to improve poor posture during sleep in either the supine position or lateral-lying position.

SUMMARY OF THE INVENTION

The present invention is a novel and unique spinal support and stretch pillow system. The uniqueness of the present invention spinal support and stretch pillow system is that it offers a distinct, adjustable support for sleeping in either a supine position or a lateral position.

The spinal support and stretch pillow system can be laid over a conventional mattress or any suitable surface such as a floor. The pillow system is comprised of a bottom liner pad, a cervical and spinal support pad, a height adjustment pad, an adjustable shoulder support, an adjustable thoracic and lumbar support pad, and a top support pad. The bottom liner pad is used as a container to retain the components of the pillow system and for covering the user's legs and feet. The cervical and spinal support pillow includes a cervical section and a tapered spinal section. The cervical section has a U-shaped cutout area for allowing the user's head to fall back therein and stretch the user's neck. The tapered spinal section has a shoulder region with an upper end and a thoracic and lumbar region with a lower end. The adjustable shoulder support pad is positioned underneath the spinal section for supporting the shoulder region of the tapered spinal section of the cervical and spinal support pad. The adjustable thoracic and lumbar support pad is positioned underneath the thoracic and lumbar region of the spinal section for further supporting the user's back. The top support pad is positioned over the cervical and spinal support pad, where one end of the top support pad is folded over against itself to retain an adjustable neck support member and the other end folded underneath against itself to retain an adjustable knee support member.

It is therefore an object of the present invention to provide a spinal support and stretch pillow system that offers varying amounts of spinal support for use regardless of whether the user is in the supine position or is in a lateral-lying position.

It is an additional object of the present invention to provide a spinal support and stretch pillow system that maintains horizontal alignment of the spine and head when the user is in a lateral-lying position.

It is a further object of the present invention to provide a spinal support and stretch pillow system that can vary the amount of the head support in both the supine position and the lateral-lying position, depending upon the comfort requirements of the user.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 4 is a longitudinal cross-sectional view taken along line 4—4 of FIG. 1;

FIG. 5 is an enlarged perspective view of the attachable and removable head support pad of the present invention spinal support and stretch pillow system; and FIG. 6 is an enlarged perspective view of an expandable balloon.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
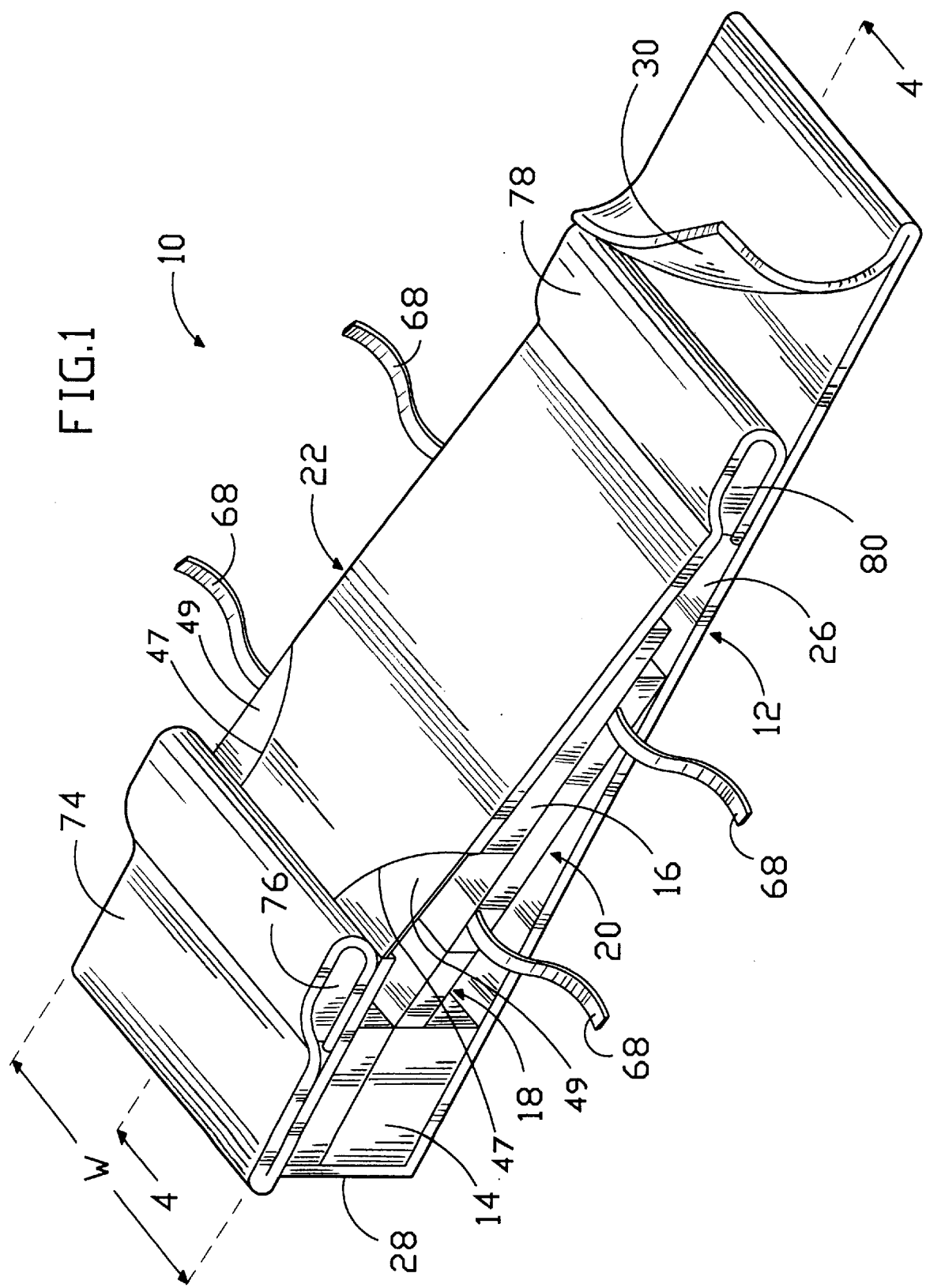
FIG. 1 is a perspective view of the preferred embodiment of the present invention spinal support and stretch pillow system.
Figure 3:
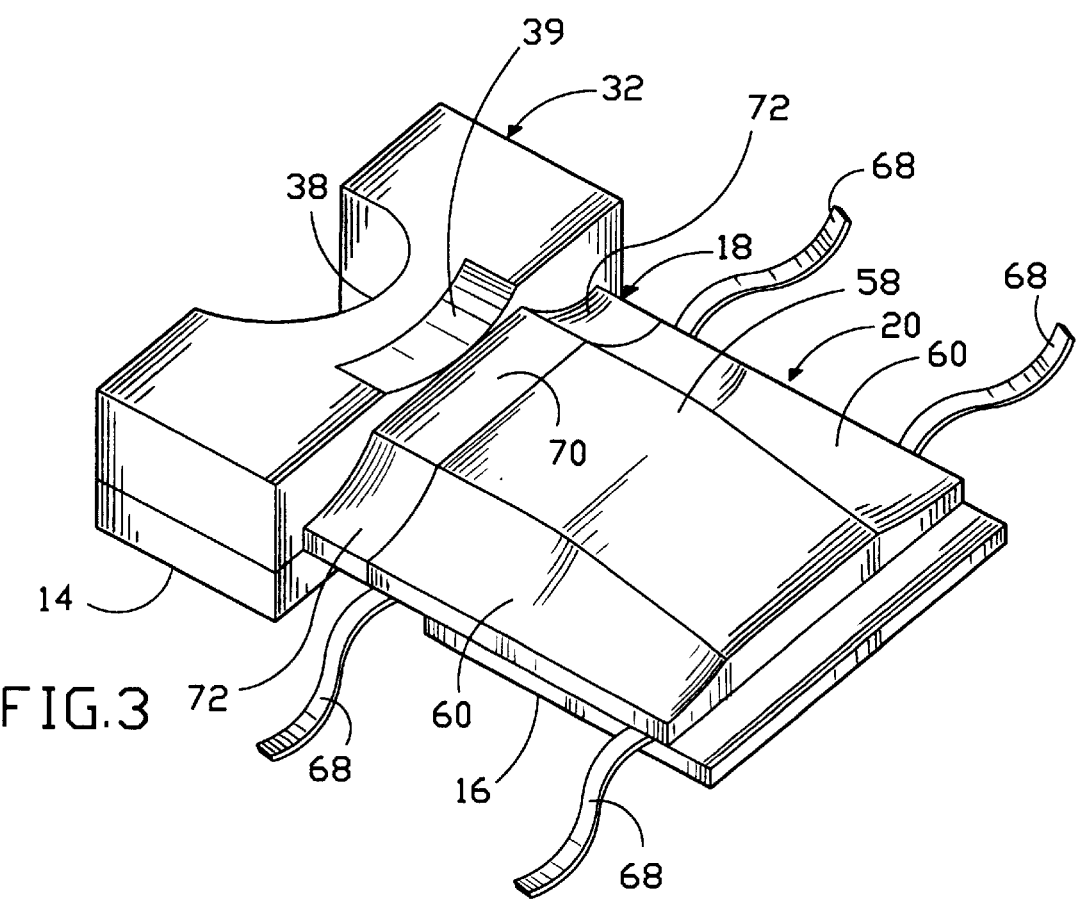
FIG. 3 is a bottom perspective view of the cervical and spinal support pad, the shoulder support pad, and the thoracic and lumbar support pad of the present invention spinal support and stretch pillow system, showing the cervical and spinal support pad parallel to a support surface.

Referring to FIGS. 1, 3 and 4, there is shown at 10 the present invention spinal support and stretch pillow system which comprises a bottom liner or container pad 12, a cervical and spinal support pad 13, an adjustable thin shoulder support pad 18, an adjustable thoracic and lumbar support pad 20, and a longitudinal elongated top cover support pad 22. The bottom liner pad 12 has a generally longitudinal elongated thin flat shaped body which has a main portion 26, a front end 28 perpendicular to the main portion 26, and a lower end 30 which is folded upwardly over for covering legs and feet of a user. The bottom liner pad 12 is made of polyester material and is a overlayer for a conventional mattress (not shown) or may be used on the floor (not shown).

Referring to FIGS. 1, 2, 3 and 4, the cervical and spinal support pad 13 includes a generally rectangular shaped cervical section 14 integrally formed with a tapered spinal section 16 for supporting the neck and spine of the user. A U-shaped cutout area 36 is provided on the cervical section 14 for allowing the user's head to fall back therein and stretch the user's neck. A height adjustment pad 32 is provided with the spinal support and stretch pillow system 10 and also has a U-shaped cutout area 38, where the adjustment pad 32 is position underneath the cervical section 14 of the cervical and spinal support pad 13 such that the cutout area 38 is aligned with and corresponds to the U-shaped cutout area 36 of the cervical section 14 (see FIG. 2). A depression 39 is provided on the back side of the height adjustment pad 32. The cervical and spinal support pad 13 and the height adjustment pad 32 are made of resilient material, such as synthetic foam material selected from various such foams in current use for similar applications, to stretch the user's neck and provide comfort. The cervical and spinal support pad 13 is positioned on and located adjacent to the front end 28 of the bottom liner pad 12.

Figure 2:
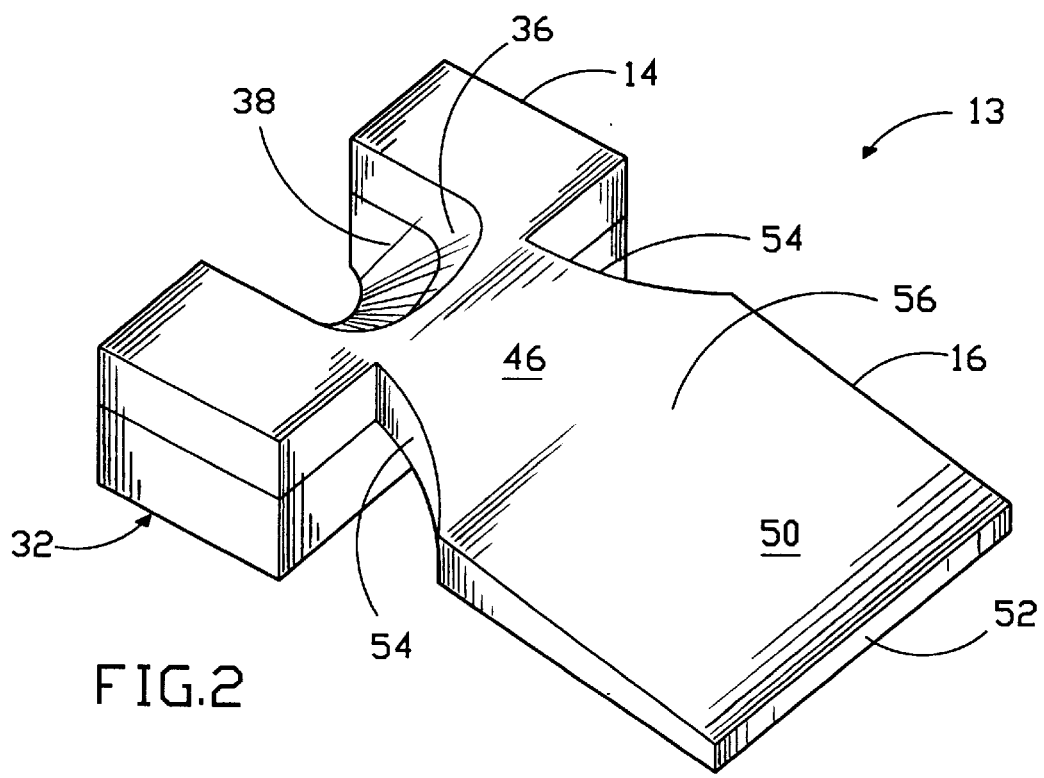
FIG. 2 is a top perspective view of the cervical and spinal support pad of the present invention spinal support and stretch pillow system, showing an inclined condition.

The tapered spinal section 16 has a shoulder region 46 with an upper end integrally formed with the cervical section 14 and a thoracic and lumbar region 50 with a lower end 52. The shoulder region 46 has two opposite cut-away curved sides 54 which extend inwardly toward a longitudinal central region 56. The upper end decreases in thickness toward the lower end 52 as shown in FIG. 2. The spinal section 16 of the cervical and spinal support pad 13 provides correct spinal alignment in a lateral sleeping position.

Referring to FIGS. 2 and 3, the cervical and spinal support pad 13 can be used in two orientations. The first orientation is with the spinal section 16 at in inclined condition (see FIG. 2). In this orientation, it provides mild stretching of the spine. The second orientation is with the spinal section 16 positioned parallel to the mattress or floor. In this orientation, it provides increased stretching by permitting the user's head to fall farther back into the cutout area 38 of the height adjustment pad 32 (see FIG. 3). In this orientation, the adjustable thin shoulder support pad 18 and the adjustable thoracic and lumbar support pad 20 can be used with the cervical and spinal support pad 13. However, it will be appreciated that the cervical and spinal support pad 13 can be used without the pad 18 mentioned above.

Referring to FIGS. 2, 3, 4 and 5, there is shown an attachable and removable head support pad 40 which is made of resilient material, such as synthetic foam, and is positioned into and attached to the U-shaped cutouts 36 and 38 of the cervical section 14 and the height adjustment pad 32 by conventional means, such as Velcro® type fasteners (not shown). The head support pad 40 has a height which is lower than the height of the cervical section 14 and provides additional support for the user's head and to provide comfort and ease of sleep. The head support pad 40 further has an expandable balloon portion 42 which is attached to a bottom of the head support pad 40. The expandable balloon portion 42 can be expanded to increase the height of the head support pad 40 for adjusting the height of the user's head. The expandable balloon portion 42 can be inflated by a conventional compressor or any conventional means known to one skilled in the art, through a valve 44 which is connected to the balloon portion 42.

Referring again to FIGS. 1, 3 and 4, there is shown the adjustable thoracic and lumbar support pad 20 which is made of resilient material such as synthetic foam, and is positioned underneath the spinal section 16 of the cervical and spinal support pad 13 for providing adjustable support to the lumbar region 50 of the spinal section 16. The thoracic and lumbar support pad 20 has a generally tapered body which decreases in thickness from a front end 62 to a lower end 64. The thoracic and lumbar support pad 20 has a longitudinal central portion 58 and two opposite tapered sides 60 which decrease in thickness extending outwardly from the central portion 58. The tapered sides 60 provide alignment of the spine when the user is sleeping in a lateral-lying position. The thoracic and lumbar support pad 20 is enclosed by a low-friction cloth material 66 to minimize sliding movement underneath the spinal section 16 of the cervical and spinal support pad 13. The thoracic and lumbar support pad 20 has a length which is shorter than the length of the spinal section 16 of the cervical and spinal support pad 13 to allow adjustment for a proper fit in the lower lumbar region and to achieve the most natural curvature of the spine for people of various heights. The shorter length of the thoracic and lumbar support pad 20 will allow a user to position the pad 20 to provide for varying support to address different needs in the lumbar region, as many people suffer from varying degrees of lower back problems. The thoracic and lumbar support pad 20 is not attached to anything so that it can be adjusted in the longitudinal direction for different users. Four straps 68 are provided and attached to the four corners of the cloth material 66 for providing easy accessibility and control when adjustment is required.

The shoulder support pad 18 is made of resilient material, such as synthetic foam, and is positioned underneath the spinal section 16 to avoid excessive stretching of the lower spine when the spinal support and stretch pillow system 10 is in the inverted position (see FIG. 3). The shoulder support pad 18 has a central portion 70 and two opposite tapered sides 72 which decrease in thickness extending outwardly from the central portion 70. The shoulder support pad 18 may further have adjustable straps (not shown) for preventing it from moving.

Referring to FIGS. 1, 4, 5 and 6, there is shown the top cover support pad 22 which is made of resilient material, such as polyester material. The support pad 22 is positioned on top of the cervical and spinal support pad 13. The top cover support pad 22 has a top end 74 which is folded over itself to retain an adjustable neck support member 76 and a bottom end 78 which is folded underneath itself to retain an adjustable knee support member 80. Each of the support members 76 and 80 includes a foam insert portion 82 and an expandable balloon portion 84 for providing extra support to the neck and knee respectively. The expandable balloon portion 84 can be inflated by a conventional compressor or any conventional means known to one skilled in the art, through a valve 90, that is similar to the valve 44 shown in FIG. 5, which is connected to the balloon portion 84. The top cover support pad 22 further includes two opposite cut-away curved recesses 47 which are located with and aligned with the two opposite cut-away sides 54 on the spinal section 16 of the cervical and spinal support pad 13. Spandex material 49 are stitched to the two opposite cut-away curved recesses 47 for providing support to the shoulder area of the user.

The present invention has many advantageous features including: (a) it offers varying amounts of spine support for a user regardless of whether the user is in the supine position or whether the user is lateral-lying position; (b) it maintains horizontal alignment of the spine and head when the user is lateral-lying position; and (c) it provides varying amounts of head support in both the lateral-lying and supine positions, depending upon the comfort requirements of the user.

By way of example, the lengths of "$L_1$", "$L_2$", "$L_3$", "$L_4$", "$L_5$", "$L_6$", and "$L_7$" are approximately 78 inches, 10 inches, 3 inches, 13½ inches, 17 inches, 14 inches, and 47 inches respectively. By way of example, the thickness "T" is approximately 4½ inches. By way of example, the width "W" of the spinal support and stretch pillow system is approximately 32 inches. It will be appreciated that the dimensions described above are merely one illustrative embodiment, and it is within the spirit and scope of the present invention to include many other comparable sets of dimensions.

The present invention conforms to conventional forms of manufacture or any other conventional way known to one skilled in the art. The present invention spinal support and stretch pillow system 10 can be used with or without the shoulder support pad 18.

Defined in detail, the present invention is a spinal and stretch pillow system for supporting and stretching a person, the system comprising: (a) a longitudinal elongated bottom liner pad having a lower end folded upwardly over and against itself for covering the person's legs and feet; (b) a cervical and spinal support pad made of resilient material and positioned and located on the bottom liner pad adjacent to an upper end of the bottom liner pad, the cervical and spinal support pad having a cervical section and a tapered spinal section integrally formed, the cervical section having a U-shaped cutout for allowing the person's head to fall back and stretching the person's neck, the tapered spinal section having a shoulder region with an upper end and a thoracic and lumbar region with a lower end, the shoulder region having two opposite recesses extending inwardly toward a longitudinal central region of the tapered spinal section, and the upper end decreasing in thickness toward the lower end; (c) a height adjustment pad made of resilient material and located underneath the cervical section of the cervical and spinal support pad and having a U-shaped cutout which is located and aligned with the U-shaped cutout of the cervical section of the cervical and spinal pad; (d) an adjustable thoracic and lumbar support pad made of resilient material and located underneath the spinal section of the cervical and spinal support pad for further supporting the person's back, the thoracic and lumbar support pad having a longitudinal central portion and two opposite tapered sides extending outwardly therefrom; and (e) an elongated top support pad made of polyester material positioned over the cervical and spinal support pad and having one end folded over against itself to retain an adjustable neck support member and the other end folded underneath against itself to retain an adjustable knee support member.

Defined broadly, the present invention is a spinal and stretch pillow system for supporting and stretching a person's body, the system comprising: (a) a cervical pad made of resilient material for supporting the person's neck and having a cutout for allowing the person's head to fall back and stretching the person's neck; (b) a spinal pad integrally formed with the cervical pad and having a shoulder region with an upper end and a thoracic and lumbar region with a lower end, the shoulder region having two opposite side recesses extending inwardly toward a central portion, and the upper end decreasing in thickness toward the lower end; (c) a height adjustment pad made of resilient material and having a cutout, the height adjustment pad located adjacent to the cervical pad such that the cutout is aligned with the cutout of the cervical pad; (d) an adjustable thoracic and lumbar support pad made of resilient material and located underneath the spine support section for further supporting the back of the human body, the thoracic and lumbar support pad having a longitudinal central portion and two opposite tapered portions extending outwardly therefrom; and (e) an elongated top support pad made of polyester material positioned over the cervical and spine pad and having one end folded over against itself to retain an adjustable neck support member and the other end folded underneath against itself to retain an adjustable knee support member.

Defined more broadly, the present invention is a pillow system for supporting and stretching a person, comprising: (a) a cervical pad for supporting the person's neck and having a cutout for allowing the person's head to fall back and stretching the person's neck; (b) a spine pad attached to the cervical pad for supporting the person's back; (c) a height adjustment pad located adjacent to the cervical pad for providing additional support to the person's neck and having a cutout which is aligned with the cutout of the cervical pad; and (d) a thoracic and lumbar support pad located adjacent to the spine pad for further supporting the person's back.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A spinal and stretch pillow system for supporting and stretching a person, the system comprising:
   a. a longitudinal elongated bottom liner pad having a lower end folded upwardly over and against itself for covering the person's legs and feet;
   b. a cervical and spinal support pad made of resilient material and positioned and located on said bottom liner pad adjacent to an upper end of said bottom liner pad, the cervical and spinal support pad having a cervical section and a tapered spinal section integrally formed, the cervical section having a U-shaped cutout for allowing the person's head to fall back and stretching the person's neck, the tapered spinal section having a shoulder region with an upper end and a thoracic and lumbar region with a lower end, the shoulder region having two opposite recesses extending inwardly toward a longitudinal central region of the tapered spinal section, and the upper end decreasing in thickness toward the lower end;
   c. a height adjustment pad made of resilient material and located underneath said cervical section of said cervical and spinal support pad and having a U-shaped cutout which is located and aligned with said U-shaped cutout of said cervical section of said cervical and spinal pad;
   d. an adjustable thoracic and lumbar support pad made of resilient material and located underneath said spinal section of said cervical and spinal support pad for further supporting the person's back, the thoracic and lumbar support pad having a longitudinal central portion and two opposite tapered sides extending outwardly therefrom; and
   e. an elongated top support pad made of polyester material positioned over said cervical and spinal support pad and having one end folded over against itself to retain an adjustable neck support member and the other end folded underneath against itself to retain an adjustable knee support member.

2. The spinal and stretch pillow system in accordance with claim 1 further comprising an attachable and removable head support pad made of resilient foam material and positioned within said U-shaped cutout portions of said cervical section of said cervical and spinal support pad and said height adjustment pad for providing additional support to the person's head.

3. The spinal and stretch pillow system in accordance with claim 2 wherein said head support pad comprises an air-tight expandable balloon attached to a bottom of said head support pad for increasing the height of said head support pad to further provide additional support to the person's head.

4. The spinal and stretch pillow system in accordance with claim 1 wherein said adjustable neck support member includes a foam insert portion and an expandable balloon portion, where the balloon portion is inflatable to increase the height of said neck support member.

5. The spinal and stretch pillow system in accordance with claim 1 wherein said adjustable knee support member includes a foam insert portion and an expandable balloon portion, where the balloon portion is inflatable to increase the height of said knee support member.

6. The spinal and stretch pillow system in accordance with claim 1 wherein said resilient material includes foam material.

7. The spinal and stretch pillow system in accordance with claim I further comprising an adjustable shoulder support pad made of resilient material for supporting said shoulder region of said spinal section of said cervical and spinal support pad, the adjustable shoulder support pad having a central portion and two opposite tapered sides extending outwardly from the central portion.

8. A spinal and stretch pillow system for supporting and stretching a person's body, the system comprising:
   a. a cervical pad made of resilient material for supporting the person's neck and having a cutout for allowing the person's head to fall back and stretching the person's neck;

b. a spinal pad integrally formed with said cervical pad and having a shoulder region with an upper end and a thoracic and lumbar region with a lower end, the shoulder region having two opposite side recesses extending inwardly toward a central portion, and the upper end decreasing in thickness toward the lower end;

c. a height adjustment pad made of resilient material and having a cutout, the height adjustment pad located adjacent to said cervical pad such that the cutout is aligned with said cutout of said cervical pad;

d. an adjustable thoracic and lumbar support pad made of resilient material and located underneath said spine support section for further supporting the back of the human body, the thoracic and lumbar support pad having a longitudinal central portion and two opposite tapered portions extending outwardly therefrom; and e. an elongated top support pad made of polyester material positioned over said cervical and spine pads and having one end folded over against itself to retain an adjustable neck support member and the other end folded underneath against itself to retain an adjustable knee support member.

9. The spinal and stretch pillow system in accordance with claim 8 further comprising a longitudinal elongated liner pad having a lower end folded upwardly over and against itself for covering the person's legs and feet.

10. The spinal and stretch pillow system in accordance with claim 8 further comprising an attachable and removable head support pad made of resilient foam material and located within said cutouts of said cervical pad and said height adjustment pad for providing additional support to the person's head.

11. The spinal and stretch pillow system in accordance with claim 10 wherein said head support pad comprises an air-tight expandable balloon attached to a bottom of said head support pad for increasing the height of said head support pad to further provide additional support to the persons' head.

12. The spinal and stretch pillow system in accordance with claim 8 wherein said adjustable neck support member includes a foam insert portion and an expandable balloon portion, where the balloon portion is inflatable to increase the height of said neck support member.

13. The spinal and stretch pillow system in accordance with claim 8 wherein said adjustable knee support member includes a foam insert portion and an expandable balloon portion, where the balloon portion is inflatable to increase the height of said knee support member.

14. The spinal and stretch pillow system in accordance with claim 8 wherein said resilient material includes foam material.

15. The spinal and stretch pillow system in accordance with claim 8 further comprising an adjustable shoulder support pad made of resilient material for supporting said shoulder region of said spinal pad and having a central portion and two opposite tapered sides extending outwardly from the central portion.

16. A pillow system for supporting and stretching a person, comprising:

a. a cervical pad for supporting the person's neck and having a cutout for allowing the person's head to fall back and stretching the person's neck;

b. a spine pad attached to said cervical pad for supporting the person's neck;

c. a height adjustment pad located adjacent to said cervical pad for providing additional support to the person's neck and having a cutout which is aligned with said cutout of said cervical pad;

d. a thoracic and lumbar support pad located adjacent to said spine pad for further supporting the person's back; and e. a bottom liner pad with a lower end folded upwardly over and against itself for covering the person's legs and feet.

17. A pillow system for supporting and stretching a person, comprising:

a. a cervical pad for supporting the person's neck and having a cutout for allowing the person's head to fall back and stretching the person's neck;

b. a spine pad attached to said cervical pad for supporting the person's back;

c. a height adjustment pad located adjacent to said cervical pad for providing additional support to the person's neck and having a cutout which is aligned with said cutout of said cervical pad;

d. a thoracic and lumbar support pad located adjacent to said spine pad for further supporting the person's back; and e. a head support pad made of resilient foam material and positioned within said cutouts of said cervical pad and said height adjustment pad for providing additional support to the person's head.

18. The pillow system in accordance with claim 17 wherein said head support pad comprises an air-tight expandable balloon attached to a bottom of said head support pad for increasing the height of said head support pad to further provide additional support to the person's head.

19. A pillow system for supporting and stretching a person, comprising:

a. a cervical pad for supporting the person's neck and having a cutout for allowing the person's head to fall back and stretching the person's neck;

b. a spine pad attached to said cervical pad for supporting the person's back;

c. a height adjustment pad located adjacent to said cervical pad for providing additional support to the person's neck and having a cutout which is aligned with said cutout of said cervical pad, d. a thoracic and lumbar support pad located adjacent to said spine pad for further supporting the person's back; and e. a top support pad made of polyester material located adjacent to said cervical pad and said spinal pad and having one end folded over against itself to retain an adjustable neck support member and the other end folded underneath against itself to retain an adjustable knee support member.

20. The pillow system in accordance with claim 19 wherein said adjustable neck support member includes a foam insert portion and an expandable balloon portion, where the balloon portion is inflatable to increase the height of said neck support member.

21. The pillow system in accordance with claim 19 wherein said adjustable knee support member includes a foam insert portion and an expandable balloon portion, where the balloon portion is inflatable to increase the height of said knee support member.

22. The pillow system in accordance with claim 16 or 17 or 19 further comprising an adjustable shoulder support pad made of resilient foam material for supporting a shoulder region of said spinal pad and having a central portion and two opposite tapered sides extending outwardly from the central portion.

23. The pillow system in accordance with claim 16 or 17 or 19 wherein said thoracic and lumbar support pad has a central portion and two opposite tapered sides extending outwardly therefrom.

* * * * *